(12) United States Patent
Iwai et al.

(10) Patent No.: US 6,946,138 B2
(45) Date of Patent: Sep. 20, 2005

(54) DILATANT COMPOSITION

(75) Inventors: Hidetaka Iwai, Tokyo (JP); Tomohiko Sano, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/123,246

(22) Filed: Apr. 17, 2002

(65) Prior Publication Data

US 2003/0077299 A1 Apr. 24, 2003

(30) Foreign Application Priority Data

Apr. 18, 2001 (JP) ......................... 2001-119843

(51) Int. Cl.$^7$ ............................. A61K 7/00; A61K 9/00; B01F 3/08
(52) U.S. Cl. ......................... 424/401; 424/400; 516/53
(58) Field of Search .................... 424/400, 401; 516/53

(56) References Cited

U.S. PATENT DOCUMENTS

| | | | |
|---|---|---|---|
| 4,798,682 A | * | 1/1989 | Ansmann ..................... 516/75 |
| 5,296,166 A | * | 3/1994 | Leong ......................... 516/43 |
| 5,869,070 A | | 2/1999 | Dixon et al. |
| 6,004,566 A | * | 12/1999 | Friedman et al. ........... 424/400 |
| 6,440,431 B1 | * | 8/2002 | Yoshida et al. ............. 424/401 |

FOREIGN PATENT DOCUMENTS

| | | |
|---|---|---|
| JP | 05-237367 | 9/1993 |
| JP | 10-182403 | 7/1998 |

\* cited by examiner

*Primary Examiner*—Gary Kunz
*Assistant Examiner*—Marina Lamm
(74) *Attorney, Agent, or Firm*—Oblon, Spivak, McClelland, Maier & Neustadt, P.C.

(57) ABSTRACT

A dilatant composition comprises (A) an o/w emulsion comprising an ionic surfactant, a water phase, and an oil phase which comprises a ceramide or a linear or branched, saturated or unsaturated $C_{12}$–$C_{32}$ fatty acid, wherein the oil phase is in a form of oil droplets having an average droplet size of from 0.01 to 0.2 $\mu$m; and (B) a nonionic, water-soluble polymer having an average molecular weight of at least 300,000.

The dilatant composition according to the present invention is excellent in dilatancy that its viscosity is low when left over standstill but increases abruptly when an external force of a certain intensity or higher is applied, and is useful in a wide variety of fields, e.g., cosmetic preparations such as humectants and massaging aids, shock absorbing agents and materials applied to around automotive crankcases.

20 Claims, No Drawings

DILATANT COMPOSITION

BACKGROUND OF THE INVENTION

1. Field of the Invention

This invention relates to compositions, which show dilatancy and are useful for cosmetic preparations, shock absorbing agents and the like.

2. Description of the Related Art

Dilatant compositions are widely used as shock absorbing agents, automotive clutch fluids and the like owing to the physical property that their viscosities increase instantaneously upon application of a shock sufficient to cause a certain degree of strain or greater but drop to the initial levels after an elapse of a certain time. Dilatant compositions are also utilized in the field of cosmetics by the flow behavior that the state of each dilatant composition changes in the order of liquid → gel → liquid by a strain, different from a gel composition the viscosity of which remains constant irrespective of a strain. JP 10-182403 A and JP 5-237767 A disclose dilatant compositions for cosmetics using water-swelling clay minerals.

Solutions of water-soluble polymers, on the other hand, generally have non-Newtonian properties, and are applied to paints having pseudoplasticity and also to toothpastes, inks, cosmetic creams and the like all of which have thixotropy. Especially for emulsified compositions, such water-soluble polymer solutions are used for thixotropic gel composition to improve emulsification stability, viscosity control and the like by protective colloidal action.

SUMMARY OF THE INVENTION

An object of the present invention is to provide a dilatant composition having a certain flow behavior totally different from conventional gel compositions which contains a water-soluble polymer (in the form of an aqueous solution).

The present inventor has found that a combination of a specific o/w (oil-in-water) emulsion and a particular water-soluble polymer can provide a composition having so-called dilatancy that its viscosity increases abruptly upon application of external force of a certain intensity or higher but drops to the initial level after removal of the external force and further that such compositions can be suitable for components in humectants or massaging aids, shock absorbing agents or materials applied around automobile crankcases.

The present invention, therefore, provides a dilatant composition comprising the following components (A) and (B):

(A) an o/w emulsion comprising an ionic surfactant, a water phase, and an oil phase comprising a ceramide or a linear or branched, saturated or unsaturated $C_{12}$–$C_{32}$ fatty acid, wherein the oil phase is in a form of oil droplets having an average droplet size of from 0.01 to 0.2 µm; and (B) a nonionic, water-soluble polymer having an average molecular weight of at least 300,000.

It is to be noted that each designation of "%" as used herein, unless otherwise specifically indicated, means "wt. %" (hereinafter simply described "%") and is a value calculated assuming that the corresponding dilatant composition is 100%

The dilatant composition according to the present invention is excellent in dilatancy that its viscosity is low when left standstill but increases abruptly when an external force of a certain intensity or higher is applied, and is useful in a wide variety of fields, e.g., cosmetics such as humectants and massaging aids, shock absorbing agents and materials applied to around automotive crankcases.

DETAILED DESCRIPTION OF THE INVENTION AND PREFERRED EMBODIMENTS

The term "dilatancy" as used herein means that, when a strain (displacement amplitude) is caused to increase continuously under a constant frequency, a localized increase is observed in storage elasticity modulus (elasticity term) at a certain degree of strain and higher. Specifically, it means that in a dynamic strain sweep of a composition, an increase (ΔG') is recognized in storage elasticity modulus (elasticity term) in a strain range of 100% and higher.

An o/w emulsion used as a component (A) in the present invention comprises an ionic surfactant, a water phase, and an oil phase comprising a ceramide or a fatty acid.

The ionic surfactant contained is selected from an anionic surfactant, a cationic surfactant or an amphoteric surfactant, and preferably contains a $C_{10}$–$C_{24}$, especially $C_{12}$–$C_{18}$ alkyl or alkenyl group as a hydrophobic group.

Examples of the anionic surfactant are higher fatty acid salts such as sodium laurate and potassium palmitate; alkyl sulfate salts such as sodium lauryl sulfate, potassium lauryl sulfate and sodium cetyl sulfate; alkyl ether sulfate salts such as triethanolamine POE lauryl sulfate; N-acylsurcosinate salts such as sodium lauroyl sarcosinate; higher fatty acid amide sulfonate salts such as sodium N-methyl-N-myristoyl taurate and sodium N-stearoyl-N-methyl taurate; phosphate ester salts such as sodium monostearyl phosphate, sodium POE oleyl ether phosphate and sodium POE stearyl ether phosphate; sulfosuccinate salts such as sodium di-2-ethylhexyl-sulfosuccinate; alkylbenzenesulfonates such as sodium linear dodecyl benzenesulfonate and triethanolamine linear dodecyl benzenesulfonate; and N-acylglutamate salts such as monosodium N-lauroylglutamate, disodium N-stearoylglutamate and monosodium N-myristoyl-L-glutamate.

Examples of the cationic surfactant are alkyl trimethyl ammonium salts such as stearyl trimethyl ammonium chloride, lauryl trimethyl ammonium chloride and cetyl trimethyl ammonium chloride; dialkyl dimethyl ammonium salts; trialkyl methyl ammonium salts; and alkylamine salts.

Examples of the amphoteric surfactant are imidazoline-based amphoteric surfactants such as 2-undecyl-N,N-(hydroxyethylcarboxymethyl)-2-imidazoline sodium and 2-cocoyl-2-imidazolinium hydroxide-1-carboxyethyloxy disodium; betaine-based amphoteric surfactants such as 2-heptadecyl-N-carboxymethyl-N-hydroxyethylimidazolinium betaine, lauryldimethylaminoacetic acid betaine, alkyl betaines, amidobetaines and sulfobetaines; and amino-acid-type amphoteric surfactants such as N-lauryl glycine, N-lauryl β-alanine and N-stearyl β-alanine.

Preferred ionic surfactants are higher fatty acid amide sulfonate salts, N-acylglutamate salts, alkyl sulfate salts, and alkyl trimethyl ammonium salts.

In the o/w emulsion, two or more ionic surfactants may be used in combination. The ionic surfactant may preferably be contained in an amount of from 0.05 to 30%, preferably 0.05 to 10%.

The oil phase in the o/w emulsion contains the ceramide or the fatty acid.

Examples of the ceramide can include aliphatic amide derivatives represented by the following formula (1) or (2):

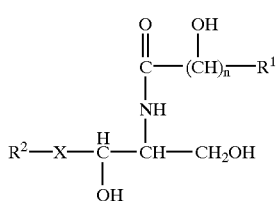

(1)

wherein $R^1$ represents a $C_{12}$–$C_{32}$ hydrocarbon group, $R^2$ represents a $C_{10}$–$C_{26}$ hydrocarbon group, X represents a single bond, —CH(OR$^3$)—, —CH=CH— or —OCH$_2$— in which $R^3$ represents H or —COCH(OH)—R$^1$, and n stands for 0 or 1, or

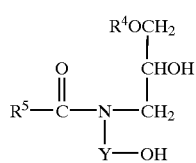

(2)

wherein $R^4$ represents a $C_{10}$–$C_{26}$ hydrocarbon group, $R^5$ represents a $C_9$–$C_{25}$ hydrocarbon group, and Y represents —(CH$_2$)$_m$— in which m stands an integer of from 2 to 6.

Examples of the compounds of the formula (1) can include natural ceramides I to VI. Examples of the compounds of the formula (2), on the other hand, can include synthetic ceramides such as N-(2-hydroxy-3-hexadecyloxypropyl)-N-2-hydroxy-ethylhexadecanamide and N-(2-hydroxy-3-hexadecyloxypropyl)-N-2-hydroxyethyldecanamide.

The fatty acid in the oil phase is a linear or branched, saturated or unsaturated $C_{12}$–$C_{32}$ fatty acid. Examples of the fatty acid are saturated $C_{12}$–$C_{24}$ fatty acids such as lauric acid, myristic acid, palmitic acid, stearic acid and behenic acid; branched $C_{12}$–$C_{32}$ fatty acids such as isostearic acid and ante-isostearic acid; and unsaturated $C_{12}$–$C_{24}$ fatty acids such as α-linoleic acid, linoleic acid, oleic acid, eicosatrienoic acid, eicosapentanoic acid, and aracidonic acid.

Two or more of these ceramides and fatty acids may be used in combination. The ceramide or fatty acid may be contained in an amount of from 0.01 to 60%, preferably 0.05 to 50% in the o/w emulsion.

In the o/w emulsion, the oil phase may also contain an aliphatic amine derivative, including a sphingosine, in addition to the ceramide or fatty acid. Examples of the aliphatic amine derivative are sphingosines disclosed in JP 6-271446A, and their derivatives disclosed in JP 6-271447A, JP 6-271448A, JP 5-194185 A and so on. Among these, preferred are sphingosines as well as the amine compounds and acid addition salts thereof disclosed in JP 5-194185 A, wherein the amine compounds are represented by the following formula (3):

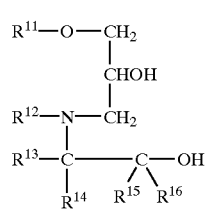

(3)

wherein $R^{11}$ represents a $C_4$–$C_{40}$ hydrocarbon group, and $R^{12}$, $R^{13}$, $R^{14}$, $R^{15}$ and $R^{16}$ each independently represents a hydrogen atom or a $C_1$–$C_{10}$ hydrocarbon group which may be substituted by one or more hydroxyl groups.

Examples of the sphingosines are sphingosine, dihydrosphingosine, phytosphingosine, dehydrosphingosine, dehydrophytosphingosine, sphingadienine, and N-methyl or N,N-dimethyl derivatives thereof. Examples of the compounds of the formula (3) can include 1-(2-hydroxyethylamino)-3-isostearyloxy-2-propanol.

In addition, the oil phase of the o/w emulsion contains one or more oils other than the above-described ceramide or fatty acid, wherein the oil ingredients employed commonly in cosmetics are liquid, semi-solid (paste) or solid at 25° C.

Examples of the oils which are liquid at 25° C. can include hydrocarbon oils such as liquid paraffin, squalane, n-octane, n-heptane and cyclohexane; ether oils such as dioctyl ether, ethylene glycol monolauryl ether, ethylene glycol dioctyl ether and glycerol monooleyl ether; ester oils such as octyldodecyl myristate, isopropyl palmitate, butyl stearate, myristyl myristate, isopropyl myristate, di-2-ethylhexyl adipate, diisopropyl sebacate, neopentyl glycol dicaprate and tricaproin; saturated higher alcohols such as isostearyl alcohol and octyldodecanol; unsaturated higher alcohols such as oleyl alcohol and lanolin alcohol; higher fatty acids such as eicosenoic acid, isomyristic acid and capric acid; higher fatty acid amides such as lauroyllaurylamine and butyl laurylamide; oils or fats such as olive oil, soybean oil and cotton seed oil; silicone oils such as dimethyl polysiloxane, cyclic dimethyl polysiloxane, methylphenyl polysiloxane, amino-modified silicones, epoxy-modified silicones, carboxyl-modified silicones, alcohol-modified silicones, alkyl-modified silicones, polyether-modified silicones and fluorine-modified silicones; and fluorine-containing oils such as perfluoroalkylethyl phosphoric acids, perfluoroalkyl polyoxyethylene phosphoric acids, perfluoropolyether and polytetrafluoroethylene.

Examples of the oils which are solid or semi-solid (paste) at 25° C. can include aliphatic alcohols. Preferred aliphatic alcohols are saturated aliphatic $C_{12}$–$C_{24}$ alcohols such as lauryl alcohol, myristyl alcohol, cetanol, stearyl alcohol and behenyl alcohol. Also usable are sterols such as cholesterol, cholesterol sulfate, polyoxyethylene cholesterol ether, stigmasterol and ergosterol.

Two or more of these oil ingredients other than the ceramides and fatty acids may be used. The o/w emulsion may contain from 2.1 to 80% of the oil phase, preferably from 2.5 to 70% as a total amount including the ceramide or fatty acid.

From the standpoint of dilatancy which can adequately provide viscoelasticity corresponding to a strain of the composition, the total amount of the ionic surfactant and oil phase in the component (A) may be from 2 to 20%, preferably from 5 to 17% in the dilatant composition.

Further, the water phase in the o/w emulsion may be in an amount of from 5 to 99.85%, preferably from 10 to 98.9%.

The o/w emulsion can be prepared by a method commonly employed by emulsifying a water phase and an oil phase with a surfactant, for example, by liquid crystal emulsification, D-phase emulsification, phase reversal temperature emulsification, or high shear emulsification using mechanical energy. High shear emulsification particularly useful for an emulsion of high concentration is particularly preferred to obtain microdroplets of oils. Preferred shear force for the emulsification is equivalent to at least 10,000 $S^{-1}$ (about 620 kg/cm$^2$), especially 10,000 to 100,000 (about 620 to 810,000 kg/cm$^2$).

Such high shear force can be obtained by use of a high-pressure emulsifying machine available from the market, for example, "FILMIX" (trade mark; manufactured by Tokushu Kika Kogyo Co., Ltd.), "CLEARMIX" (trade mark; manufactured by M. TECHNICS K. K. ), "Microfluidizer" (trade mark; manufactured by Microfluidics Corporation), "DeBEE 2000" (trade name; manufactured by B.E.E. International Corporation), or the like.

One example to obtain a suitable o/w emulsion is to set the injection pressure within a range of from 300 to 3,000 kg/cm$^2$ and the temperature within a range of from 5 to 50° C. It is, however, to be noted that the above-described operation conditions such as pressure and temperature vary depending on the specification of each apparatus and shall not be limited specifically.

Alternatively, suitable emulsion can also be obtained more efficiently by applying similar high-shear processing to a pre-emulsion obtained by a conventional emulsification method. Further, this high-shear processing may be applied repeatedly as needed.

The average size of droplets (oil droplets) emulsified and dispersed oil-phase in the o/w emulsion may range from 0.01 to 0.2 μm, preferably from 0.01 to 0.15 μm. The average droplet size is measured by the laser diffraction/scattering method.

The component (A) may preferably have a viscosity of from 200 to 1,000,000 mPa·s, especially from 2,000 to 100.000 mPa·s as measured at 25° C. by a Brookfield rotational viscometer.

The nonionic water-soluble polymer used in the component (B) of the present invention includes a water-soluble synthetic polymer and a water-soluble natural polymer.

Examples of the water-soluble synthetic polymer are polyvinyl alcohol, carboxyvinyl polymer, polyacrylamide, polyvinylpyrrolidone, polyvinyl methyl ether, polyvinylsulfone, maleic acid copolymers, polyethylene glycol, polydiallylamine, polyethylene-imine, water-soluble cellulose derivatives (e.g., carboxymethylcellulose, methylcellulose, methylhydroxypropylcellulose, hydroxyethylcellulose, hydroxypropylcellulose, sodium cellulose sulfate ester, and the like), starch derivatives (e.g., oxidized starch, dialdehyde starch, dextrin, British gum, acetylated starch, starch phosphate, carboxymethylstarch, hydroxyethylstarch, hydroxypropylstarch, and the like).

Examples of the water-soluble natural polymer are gum arabic, tragacanth gum, karaya gum, guar gum, tara gum, locust bean gum, tamarind gum, sodium alginate, propylene glycol alginate, carrageenan, pharcellulan, agar, high methoxypectin, low methoxy pectin, chitin, chitosan, starches (for example, starches, α-starches, soluble starches and other starches derived from corn, potato, wheat, rice, sweet potato, tapioca and the like), proteins (for example, sodium caseinate, gelatin, albumin and the like), chondroitin sulfate, and hyaluronic acid.

Particularly preferred nonionic water-soluble polymer of the component (B), are polyethylene glycol, carboxymethylcellulose, methylcellulose, methylhydroxypropylcellulose, hydroxyethylcellulose, hydroxyethylstarch, and hydroxypropylstarch.

Two or more of these nonionic water-soluble polymers may be used. The nonionic water-soluble polymer may be contained in an amount of from 0.05 to 1.2%, preferably from 0.1 to 0.6% in the dilatant composition.

The component (B) has an average molecular weight of at least 300,000, preferably 700,000 or higher, more preferably 1,000,000 or higher as measured at 25° C. by the intrinsic viscosity analysis.

The dilatant composition according to the present invention can further contain a variety of other ingredients that are conventionally used in cosmetics, as needed, depending on the given application type provided, combining with the components (A) and (B). For example, humectants such as polyhydric alcohols and guanidines; various active agents; and powder, fragrances, colorants, ultraviolet absorbers and preservatives are included.

Of these, polyhydric alcohols can include, among others, dihydric alcohols such as ethylene glycol, propylene glycol and 1,3-butylene glycol; trihydric alcohols such as glycerin; tetrahydric alcohols such as pentaerythritol; sugar alcohols such as glucose and sorbitol; polyhydric alcohol polymers such as polyethylene glycol (molecular weight: 200 to 2,500), diglycerin and triglycerin; alcohol alkyl ethers and alcohol ether esters.

Active agent effective for whitening, promotion of blood circulation, promotion of lipolysis and anti-inflammation can be plant extracts, amino acids, hydroxy acids, and hyaluronic acids.

Dilatant compositions according to the present invention can be used in many fields such as cosmetics, shock absorbing agents and materials applied around automotive crankcases. Especially in the field of cosmetics, they can be used as cosmetic waters, massaging aids, pack preparations, beauty liquids, plasters, cleansing preparations and the like owing to merits such that they do not drip or run off when dispensed onto the finger tips, are easily applicable to the skin and have good spreadability, and are topically applicable with ease.

In the present invention, dilatancy is measured by the following method.

Apparatus: Oscillation viscometer ("VIBRO VISCOMETER CJV-5000", trade name; manufactured by A & D Company)

Measuring temperature: 25° C.

Viscosity measurement:
  Low viscosity state A state after left over standstill for 30 minutes to 3 days.
  High viscosity state A state immediately after stirred at 3,000 rpm for 30 seconds by a vortex stirrer ("Maximix II", trade name; manufactured by Thermoline L+M).

$$\text{Dilatancy factor} = \frac{(\text{Viscosity in high-viscosity state})}{(\text{Viscosity in low-viscosity state})}$$

The term "dilatancy" as used herein means that this dilatancy factor is greater than 1, preferably 1.2 or greater, more preferably 2 or greater.

EXAMPLE 1

Each of o/w emulsions (1) to (8) was prepared by preemulsifying a batch of the corresponding formulation shown in Table 1 and then subjecting the preemulsion to emulsification three times under $9 \times 10^7$ S$^{-1}$ (2,800 kg/cm$^2$) in a high-pressure emulsifying machine "DeBEE 2000" (trade name; manufactured by B.E.E. International Corporation).

TABLE 1

| Component (A) | (1) | (2) | (3) | (4) | (5) | (6) | (7) | (8) |
|---|---|---|---|---|---|---|---|---|
| Sodium N-stearoyl-L-glutamate | 1.5 | | | | | 1.5 | 1.5 | 1.5 |
| Disodium N-stearoyl-L-glutamate | | 1.5 | | | | | | |
| Sodium N-stearoyl-N-methyl taurate | | | 1.5 | | | | | |
| Sodium cetyl sulfate | | | | 1.5 | | | | |
| Cetyl trimethyl ammonium chloride | | | | | 1.5 | | | |
| Ceramide* | 5.0 | 5.0 | 5.0 | 5.0 | 5.0 | | 5.0 | 5.0 |
| Palmitic acid | | | | | | 1.65 | | |
| Stearic acid | | | | | | 1.35 | | |
| Dimethyl polysiloxane (6 cs) | 16.4 | 16.4 | 16.4 | 16.4 | 16.4 | 16.4 | | |
| Squalane | | | | | | | 16.4 | |
| Liquid paraffin | | | | | | | | 16.4 |
| Glycerin | 18.0 | 18.0 | 18.0 | 18.0 | 18.0 | 18.0 | 18.0 | 18.0 |
| Purified water | 59.1 | 59.1 | 59.1 | 59.1 | 59.1 | 59.1 | 59.1 | 59.1 |
| Average size of emulsified droplets of oil phase (μm) | 0.051 | 0.063 | 0.066 | 0.07 | 0.051 | 0.06 | 0.057 | 0.056 |

*N-(3-hexadecyloxy-2-hydroxypropyl)-N-2-hydroxyethylhexadecanamide

On the other hand, 2% aqueous solutions of the components (B) shown in Table 2 were prepared, respectively.

Each composition was produced by mixing component (A) (5 parts by weight) in Table 1, the 2% aqueous solution of the corresponding component (B) (2 parts by weight) in Table 2, and purified water (3 parts by weight). Its dilatancy factor was measured by a method describe below. The results are also shown in Table 2.

Viscosity in a low viscosity state:
  Measured by an oscillation viscometer ("CJV-5000", trade name; manufactured by A & D Company) after left over standstill at 25° C. for 3 days.

Viscosity in a high viscosity state:
  Measured by the oscillation viscometer ("CJV-5000", trade name; manufactured by A & D Company).

TABLE 2

| No. | Component (A) | Component (B) (m.w.) | Dilatancy factor |
|---|---|---|---|
| Invention composition | | | |
| 1 | (1) | Hydroxyethylcellulose (1,300,000) | 810 |
| 2 | (2) | Hydroxyethylcellulose (1,300,000) | 188 |
| 3 | (3) | Hydroxyethylcellulose (1,300,000) | 70 |
| 4 | (4) | Hydroxyethylcellulose (1,300,000) | 400 |
| 5 | (5) | Hydroxyethylcellulose (1,300,000) | 189 |
| 6 | (6) | Hydroxyethylcellulose (1,300,000) | 195 |
| 7 | (7) | Hydroxyethylcellulose (1,300,000) | 750 |
| 8 | (8) | Hydroxyethylcellulose (1,300,000) | 728 |
| 9 | (1) | Polyethylene glycol (750,000) | 20 |
| 10 | (1) | Polyethylene glycol (2,000,000) | 425 |
| 11 | (1) | Polyethylene glycol (4,000,000) | 780 |
| 12 | (1) | Hydroxyethylcellulose (620,000) | 432 |
| 13 | (1) | Hydroxyethylcellulose (720,000) | 532 |
| 14 | (1) | Hydroxyethylcellulose (1,150,000) | 773 |
| 15 | (1) | Hydroxyethylcellulose (1,470,000) | 850 |
| Comparative composition | | | |
| 16 | (1) | Polyethylene glycol (1,540) | 1 |
| 17 | (1) | Polyethylene glycol (20,000) | 0.9 |
| 18 | (1) | Polyethylene glycol (70,000) | 1 |
| 19 | (1) | Polyethylene glycol (200,000) | 1 |
| 20 | (1) | Hydroxyethylcellulose (70,000) | 1.1 |
| 21 | (1) | Hydroxyethylcellulose (250,000) | 1 |
| 22 | (1) | Polyvinylpyrrolidone (220,0000) | 1 |

The compositions of the present invention (Nos. 1 to 15) exhibited pronounced dilatancy.

EXAMPLE 2

In a similar manner as in Example 1, the o/w emulsions (9) to (16) of the formulations shown in Table 3 were prepared under the corresponding emulsification conditions in the high pressure emulsifying machine "DeBEE 2000" (trade name; manufactured by B.E.E. International Corporation). The above emulsions were mixed with their corresponding components shown in Table 4 in a similar manner as in Example 1. Its viscosity was measured in both low-viscosity state and high-viscosity state to determine its dilatancy factor. The results are also shown in Table 4.

TABLE 3

| Component (A) | (%) | | | | | | | |
|---|---|---|---|---|---|---|---|---|
| | (9) | (10) | (11) | (12) | (13) | (14) | (15) | (16) |
| Sodium N-stearoyl-L-glutamate | 1.5 | 1.5 | 1.5 | 1.5 | 1.5 | 1.5 | 1.5 | |
| Polyoxyethylene (3) stearyl ether | | | | | | | | 1.5 |
| Ceramide* | 5.0 | 5.0 | 5.0 | 5.0 | 5.0 | | | 5.0 |
| Cetanol | | | | | | 3.0 | | |
| Stearyl alcohol | | | | | | 2.0 | | |
| Dimethyl polysiloxane | 16.4 | 16.4 | 16.4 | 16.4 | 16.4 | 16.4 | 16.4 | 16.4 |
| Glycerin | 18.0 | 18.0 | 18.0 | 18.0 | 18.0 | 18.0 | 18.0 | 18.0 |
| Purified water | 59.1 | 59.1 | 59.1 | 59.1 | 59.1 | 59.1 | 64.1 | 59.1 |
| Emulsification pressure (s$^{-1}$) | $6 \times 10^7$ | $6 \times 10^7$ | $6 \times 10^7$ | $6 \times 10^7$ | $6 \times 10^7$ | $6 \times 10^7$ | $6 \times 10^7$ | $6 \times 10^7$ |
| Average size of emulsified droplets of oil phase ($\mu$m) | 0.074 | 0.1 | 0.124 | 0.13 | 0.3 | 0.066 | 0.054 | 0.073 |

*N-(3-hexadecyloxy-2-hydroxypropyl)-N-2-hydroxyethylhexadecanamide

TABLE 4

| No. | Component (A) (emulsion) | Component (B) (m.w.) | Dilatancy factor |
|---|---|---|---|
| Invention composition | | | |
| 23 | (9) | Hydroxyethylcellulose (1,300,000) | 484 |
| 24 | (10) | Hydroxyethylcellulose (1,300,000) | 220 |
| 25 | (11) | Hydroxyethylcellulose (1,300,000) | 54 |
| 26 | (12) | Hydroxyethylcellulose (1,300,000) | 27 |

TABLE 4-continued

| No. | Component (A) (emulsion) | Component (B) (m.w.) | Dilatancy factor |
|---|---|---|---|
| Comparative composition | | | |
| 27 | (13) | Hydroxyethylcellulose (1,300,000) | 1.1 |
| 28 | (14) | Hydroxyethylcellulose (1,300,000) | 0.9 |
| 29 | (15) | Hydroxyethylcellulose (1,300,000) | 0.9 |
| 30 | (16) | Hydroxyethylcellulose (1,300,000) | 1 |

The compositions of the present invention (Nos. 23 to 26) exhibited pronounced dilatancy.

EXAMPLES 3 and 4

Essences of the formulations shown in Table 5 were produced, respectively.

TABLE 5

| Ingredient (wt. %) | Example 3 | Example 4 |
|---|---|---|
| A | | |
| (1) Monosodium N-stearoylglutamate | 0.5 | 0.5 |
| (2) Glycerin | 12.0 | 12.0 |
| (3) Ceramide* | 1.7 | 1.7 |
| (4) Dimethyl polysiloxane (6 cs) | 5.5 | 5.5 |
| (5) Methylparabene | 0.1 | 0.1 |
| (6) Fucus extract | 3.3 | 3.3 |
| (7) Purified water | 6.5 | 6.5 |
| B | | |
| (8) Hydroxyethylcellulose (m.w. 1,470,000) | 1.3 | — |
| (9) Polyethylene glycol (m.w. 1,000,000) | — | 0.7 |
| (10) Purified water | 69.1 | 69.7 |
| Average size of emulsified droplets of oil phase (μm) | 0.058 | 0.058 |
| Dilatancy factor | 815 | 255 |

*N-(3-hexadecyloxy-2-hydroxypropyl)-N-2-hydroxyethylhexadecanamide (Production Procedure)

Each essence was obtained by the following procedure. In accordance with the corresponding formula shown in Table 5, the ingredients (1) to (7) were combined and then subjected to emulsification three times under $9 \times 10^7$ s$^{-1}$ (2,800 kg/cm$^2$) by high-pressure emulsification to obtain an o/w emulsion. On the other hand, the ingredients (8) or (9) and (10) were mixed in accordance with the corresponding formula shown in Table 5 to obtain a solution of the water-soluble polymer. The o/w emulsion and the solution of the water-soluble polymer were mixed together to provide the essence.

EXAMPLE 5

A massage gel of the below-described formula was produced. The droplet size of the o/w emulsion was 0.08 μm, and the dilatancy factor of the dilatant composition was 730.

| (Ingredients) | |
|---|---|
| (1) Monosodium N-stearoyl-L-glutamate | 0.75% |
| (2) Ceramide | 2.5 |
| (3) Dimethyl polysiloxane (6 cs) | 5.0 |
| (4) Squalane | 2.5 |
| (5) Glycerin | 8.2 |
| (6) Purified water | 50.45 |
| (7) Hydroxyethylcellulose (m.w. 1,470,000) | 0.4 |
| (8) Purified water | 30.25 |

(Production Procedure)

The ingredients (1) to (6) were combined, and by high pressure emulsification, an o/w emulsion (emulsification method: emulsified three times under $9 \times 10^7$ s$^{-1}$) was obtained. On the other hand, the ingredients (7) and (8) were mixed together to obtain an aqueous solution of the water-soluble polymer. The o/w emulsion and the solution of the water-soluble polymer were mixed together to provide the massage gel of the above-described formulation.

EXAMPLE 6

A shock absorbing agent of the below-described formulation was produced. The droplet size of the o/w emulsion was 0.08 μm, and the dilatancy factor of the dilatant composition was 180.

| (Ingredients) | |
|---|---|
| (1) Cetyl trimethyl ammonium chloride | 0.75% |
| (2) Palmitic acid | 1.15 |
| (3) Stearic acid | 1.4 |
| (4) Liquid paraffin | 7.5 |
| (5) Purified water | 44.4 |
| (6) Polyethylene glycol (m.w. 4,000,000) | 0.4 |
| (7) Purified water | 44.4 |

(Production Procedure)

The ingredients (1) to (5) were combined, and by high pressure emulsification, an o/w emulsion (emulsification method: emulsified three times under $9 \times 10^7$ s$^{-1}$) was obtained. On the other hand, the ingredients (6) and (7) were mixed together to obtain an aqueous solution of the water-soluble polymer. The o/w emulsion and the solution of the water-soluble polymer were mixed together to obtain the shock absorbing agent.

What is claimed is:

1. A dilatant composition comprising:
   (A) an o/w emulsion composition comprising an ionic surfactant, a water phase, and an oil phase which comprises a ceramide or linear a or branched, saturated or unsaturated $C_{12}$–$C_{32}$ fatty acid, wherein the oil phase is in a form of oil droplets having an average droplet size of from 0.01 to 0.2 μm; and (B) a nonionic, water-soluble polymer having an average molecular weight of at least 300,000 wherein said composition exhibits a dilatancy behavior.

2. A dilatant composition according to claim 1, which has a dilatancy factor of at least 1.2.

3. The dilatant composition according to claim 1, wherein said ionic surfactant has a $C_{10}$–$C_{24}$ hydrophobic group.

4. The dilatant composition according to claim 1, wherein said o/w emulsion has been prepared by high shear emulsification.

5. The dilatant composition according to claim 1, wherein a total content of said ionic surfactant and said oil phase ranges from 2 to 20 wt. %, and a content of said water-soluble polymer ranges from 0.05 to 1.2 wt. %.

6. The dilatant composition according to claim 1, wherein said water-soluble polymer is at least one polymer selected from the group consisting of polyethylene glycol, carboxymethylcellulose, methylcellulose, methyl-hydroxy-propylcellulose, hydroxy ethylcellulose, hydroxyethylstarch and hydroxypropylstarch.

7. A cosmetic preparation comprising a dilatant composition according to claim 1 and purified water.

8. The dilatant composition according to claim 1, wherein said ionic surfactant has a $C_{12}$–$C_{18}$ hydrophobic group.

9. The dilatant composition according to claim 1, wherein said ionic surfactant is an anionic surfactant.

10. The dilatant composition according to claim 1, wherein said ionic surfactant is an cationic surfactant.

11. The dilatant composition according to claim 1, wherein said ionic surfactant is an amphoteric surfactant.

12. The dilatant composition according to claim 1, wherein said ionic surfactant is at least one member selected from the group consisting of a fatty acid amide sulfonate salt, N-acylglutamate salt, alkyl sulfate salt, and alkyl trimethyl ammonium salt.

13. The dilatant composition according to claim 1, wherein the average droplet size is from 0.01 to 0.15 μm.

14. The dilatant composition according to claim 1, wherein the dilatancy factor is least 2.

15. A method of preparing the composition according to claim 1, comprising contacting the o/w emulsion with the nonionic, water-soluble polymer.

16. The method according to claim 15, further comprising pre-emulsifying the ionic surfactant, water phase, and oil phase comprising a ceramide or fatty acid to form a pre-emulsion.

17. The method according to claim 16, further comprising emulsifying the pre-emulsion.

18. The method according to claim 17, wherein the emulsifying is performed at least three times.

19. The method according to claim 17, wherein the emulsifying is performed under high pressure conditions of at least 2,800 kg/cm².

20. A method of making a cosmetic preparation, comprising contacting the composition according to claim 1 with purified water.

* * * * *